(12) United States Patent
Scheid

(10) Patent No.: US 9,651,509 B2
(45) Date of Patent: May 16, 2017

(54) METHOD FOR INVESTIGATING EARLY LINER COLLAPSE IN A SHAPED CHARGE

(71) Applicant: The United States of America as represented by the Secretary of the Navy, Washington, DC (US)

(72) Inventor: Eric Scheid, Bloomington, IN (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 152 days.

(21) Appl. No.: 14/663,404

(22) Filed: Mar. 19, 2015

(65) Prior Publication Data

US 2015/0268041 A1 Sep. 24, 2015

Related U.S. Application Data

(60) Provisional application No. 61/955,456, filed on Mar. 19, 2014.

(51) Int. Cl.
| | | |
|---|---|---|
| G01B 21/32 | (2006.01) |
| G01N 25/50 | (2006.01) |
| F42B 1/02 | (2006.01) |
| F42B 1/032 | (2006.01) |
| F42B 35/00 | (2006.01) |

(52) U.S. Cl.
CPC .............. *G01N 25/50* (2013.01); *F42B 1/02* (2013.01); *F42B 1/032* (2013.01); *F42B 35/00* (2013.01)

(58) Field of Classification Search
CPC . F42B 1/02; F42B 35/00; F42B 1/032; G01N 33/227; G01N 3/48; G01N 25/50; G01B 21/32

USPC ................... 73/35.17, 35.14, 35.15
See application file for complete search history.

(56) References Cited

U.S. PATENT DOCUMENTS

| | | | |
|---|---|---|---|
| 2,972,247 A * | 2/1961 | Zablocki ................ | G01N 25/50 73/167 |
| 3,121,322 A | 2/1964 | Caldwell | |
| 4,222,329 A | 9/1980 | Austin | |
| 4,498,367 A * | 2/1985 | Skolnick ................. | F42B 1/032 102/306 |
| 4,760,795 A * | 8/1988 | Young ................. | F42C 19/0838 102/293 |
| 4,766,813 A | 8/1988 | Winter et al. | |
| 4,932,239 A * | 6/1990 | Regalbuto ............... | F42B 35/00 73/12.08 |
| 5,038,683 A | 8/1991 | Baker et al. | |
| 5,567,906 A | 10/1996 | Reese et al. | |
| 5,619,008 A * | 4/1997 | Chawla .................... | F42B 1/02 102/307 |
| 6,354,137 B1 * | 3/2002 | Guirguis ................. | F42B 35/00 73/35.14 |
| 6,354,219 B1 | 3/2002 | Pratt et al. | |
| 6,634,300 B2 | 10/2003 | Reese et al. | |
| 6,644,099 B2 * | 11/2003 | Bell ........................ | E21B 29/02 73/12.01 |

(Continued)

FOREIGN PATENT DOCUMENTS

CN 103335566 10/2013

*Primary Examiner* — Helen Kwok
(74) *Attorney, Agent, or Firm* — Christopher A. Monsey

(57) ABSTRACT

An apparatus and method for investigating and analyzing early shaped charge liner collapse and liner material, wherein such method uses material from an actual liner, in order to collect data on the explosive event and its impact on the material.

25 Claims, 11 Drawing Sheets

(56) References Cited

U.S. PATENT DOCUMENTS

| | | | |
|---|---|---|---|
| 6,668,726 B2 | 12/2003 | Lussier | |
| 7,261,036 B2 | 8/2007 | Bourne et al. | |
| 7,547,345 B2 | 6/2009 | Leidel et al. | |
| 7,581,498 B2 | 9/2009 | Hetz et al. | |
| 7,669,460 B1 * | 3/2010 | Sandusky | G01N 33/227 |
| | | | 73/35.16 |
| 7,954,433 B1 * | 6/2011 | Barnett | F42B 1/036 |
| | | | 102/307 |
| 8,161,799 B1 * | 4/2012 | Kim | G01N 33/227 |
| | | | 73/35.14 |
| 8,584,772 B2 | 11/2013 | Yang et al. | |
| 8,627,707 B2 * | 1/2014 | Hardesty | G01N 33/227 |
| | | | 102/306 |
| 8,701,538 B2 | 4/2014 | Marscher et al. | |
| 2003/0037692 A1 * | 2/2003 | Liu | C06B 33/00 |
| | | | 102/301 |
| 2006/0201373 A1 * | 9/2006 | Sammons | C06B 45/00 |
| | | | 102/476 |

* cited by examiner

METHOD FOR INVESTIGATING EARLY LINER COLLAPSE IN A SHAPED CHARGE

CROSS-REFERENCE TO RELATED APPLICATIONS

The present application claims the benefit of U.S. Provisional Patent Application Ser. No. 61/955,456, filed on Mar. 19, 2014, and entitled "Shaped Charge; Method for Investigating Early Liner Collapse," the complete disclosure of which is expressly incorporated by reference herein.

STATEMENT REGARDING FEDERALLY SPONSORED RESEARCH OR DEVELOPMENT

The invention described herein was made in the performance of official duties by one or more employees of the Department of the Navy and may be manufactured, used and licensed by or for the United States Government for any governmental purpose without payment of any royalties thereon. This invention (NC 103,114) is assigned to the United Stated Government and is available for licensing for commercial purposes. Licensing and technical inquiries may be directed to the Technology Transfer Office, Naval Surface Warfare Center Crane, email: Cran_CTO@navy.mil.

BACKGROUND OF THE DISCLOSURE

A need exists for a low cost and practical method to investigate and analyze early shaped charge liner collapse and the liner material after an explosive event. It is desirable to test liner material of a shaped charge after an explosive event in order to investigate the effects of subtle alterations in the liner metallurgy of the shaped charge. However, testing liner materials and/or the collapse of the liner may be difficult because liner collapse of a shaped charge is an explosive event that occurs in microseconds at speeds exceeding 17,000 miles per hour and can include pressures exceeding 30 GPa (gigapascals) and temperatures above 1000° F. While complex and expensive experiments exist for analyzing shaped charges, such as jet capture testing, flight flash X-ray images, and computer simulations, there is a need for a practical and less expensive method of investigating the effects of subtle alterations in shaped charge liner metallurgy.

For example, FIG. 1 shows three photographs of a sample of recovered liner material from a traditional jet capture test, where the liner material has undergone complete deformation, including in flight elongation. In this case, it is difficult to assess the sample because early-stage deformation is difficult to distinguish from late-stage deformation because the explosive jets fully formed, which is a process that occurs after early-stage deformation. The sample also may be broken into numerous pieces during the explosive event and, therefore, may not be usable or recoverable for metallurgical testing. In addition, there is no time history associated with the sample of the liner material. As such, analysis of early liner collapse is difficult or not possible with the traditional jet capture test.

Similarly, there are limitation associated with flight flash X-ray because this technique shows elongation of the jet in flight but does not show liner collapse and early jet formation.

Additionally, while computer simulations, such as the Hydrocodes (FIG. 2) and a CALE-generated model (FIG. 3) show approximations of early-stage liner collapse, these simulations do not physically investigate an actual sample which can be used for metallurgical testing. More particularly, the computer simulation methods of FIGS. 2 and 3 require a mathematical model to approximate interaction between the modeled structure and a shock progression. As such, none of the above methods provide physical materials representing the initial moments of collapse in shaped charge liner material that can be used to analyze the liner materials through post-explosive event tests, such as metallurgical assessments.

SUMMARY OF THE DISCLOSURE

The present invention generally relates to a testing method for analyzing liner collapse in a shaped charge and, more particularly, to a method of analyzing early-stage liner collapse in a shaped charge which produces an actual sample on which metallurgical and other testing may be performed.

In one embodiment of the present disclosure, a method of analyzing early-stage deformation of a liner of a shaped charge comprises providing a testing apparatus, coupling an explosive material to a liner material to define a shaped charged, affixing a detonator to the explosive material, assembling the shaped charge within the testing apparatus, positioning the assembled testing apparatus and shaped charge within a container of fluid and below a surface of the fluid, detonating the shaped charge, and collecting the liner material from the fluid.

In another embodiment of the present disclosure, a method of analyzing early-stage deformation of a liner of a shaped charge comprises providing a testing apparatus, providing an explosive material comprised of 1-10% explosive matter, coupling the explosive material to a liner material to define a shaped charged, affixing a detonator to the explosive material, assembling the shaped charge within the testing apparatus, detonating the shaped charge, and collecting the liner material.

Additional features and advantages of the present invention will become apparent to those skilled in the art upon consideration of the following detailed description of the illustrative embodiment exemplifying the best mode of carrying out the invention as presently perceived.

BRIEF DESCRIPTION OF THE DRAWINGS

The detailed description of the drawings particularly refers to the accompanying Figures in which.

DETAILED DESCRIPTION OF THE DRAWINGS

The embodiments of the invention described herein are not intended to be exhaustive or to limit the invention to precise forms disclosed. Rather, the embodiments selected for description have been chosen to enable one skilled in the art to practice the invention.

The present disclosure relates to a method and test fixture for analyzing shaped charge liner material after an explosive event. More particularly, the present disclosure is able to use an actual shaped charge with a small amount of explosive material which allows the liner material to be recovered after the explosive event so that testing can be performed on the liner material and early-stage deformation of the liner material may be explored.

Figure 1:
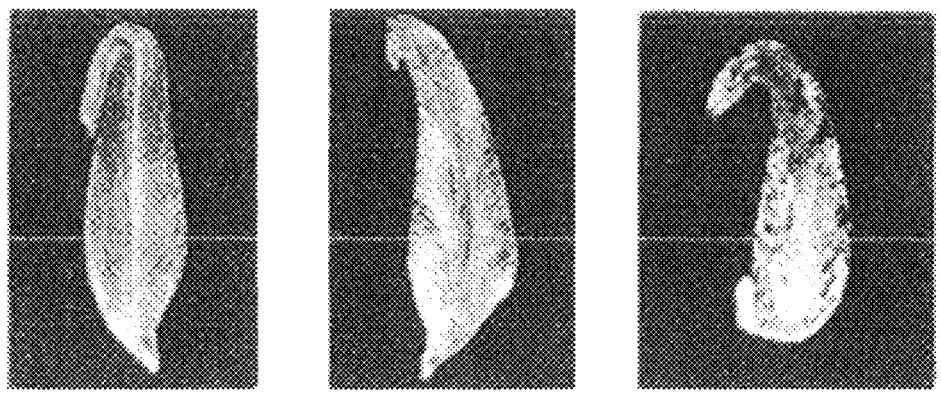
FIG. 1 shows three photographs of a sample of recovered liner material from a prior art jet capture test.
Figure 2:
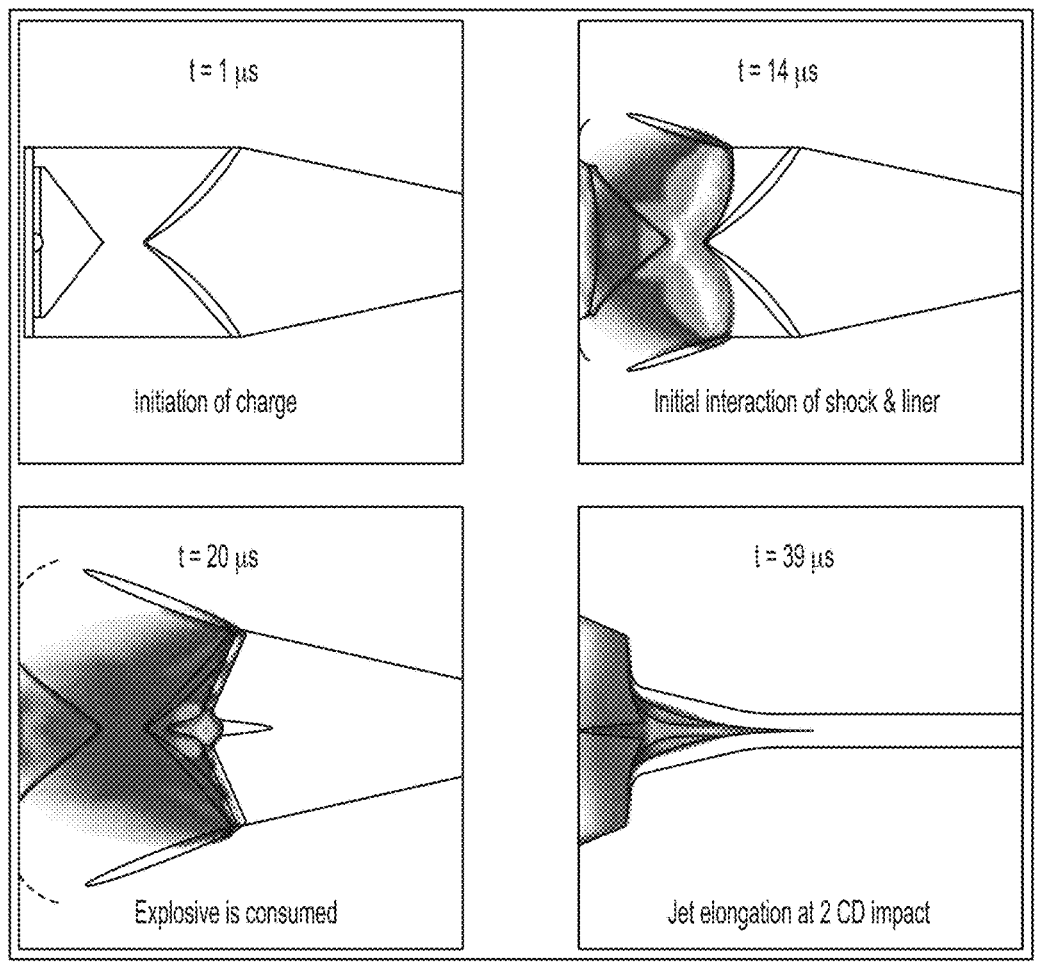
FIG. 2 shows a prior art computer simulation using Hydrocodes to generate a model of liner collapse in a shaped charge.
Figure 3:
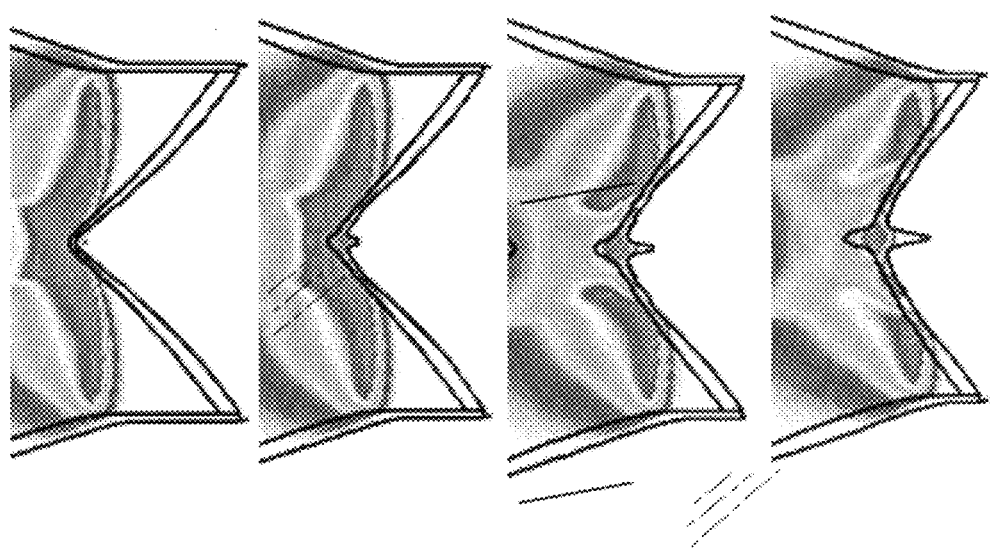
FIG. 3 shows a prior art computer simulation using CALE to generate a model of shock progression and liner collapse over the first three microseconds of shock and liner interaction.
Figure 4:
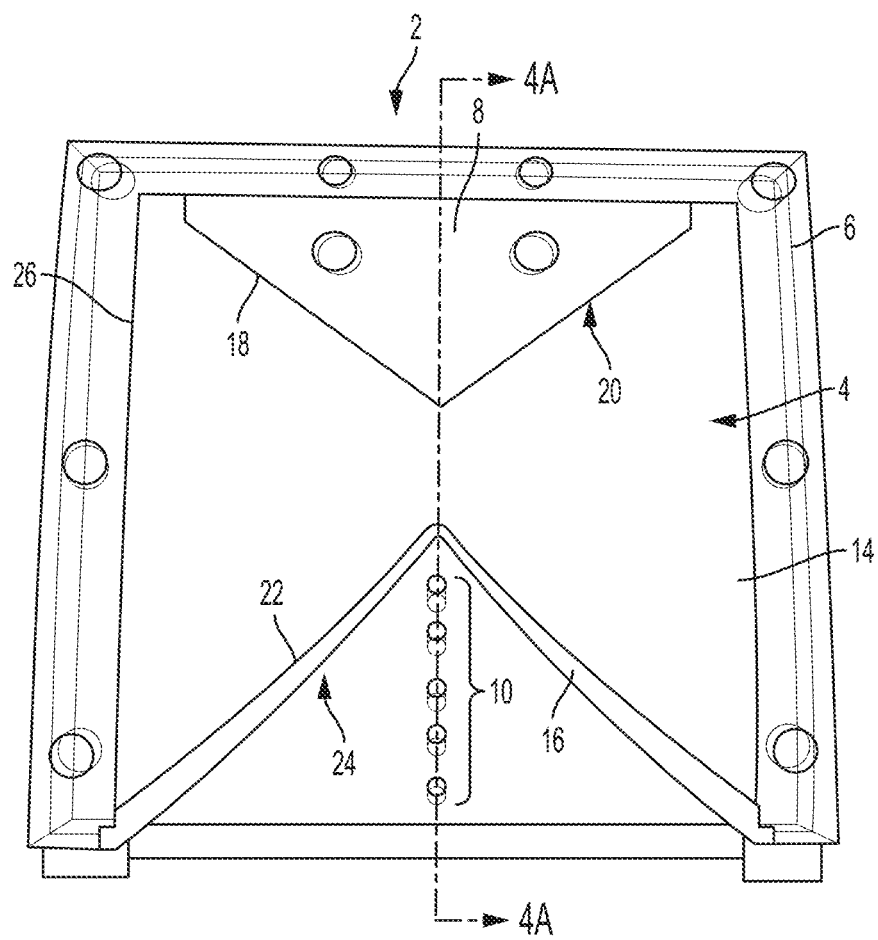
FIG. 4 is an elevational view of an exemplary two-dimensional test charge placed in an exemplary test fixture of the present disclosure.
Figure 5:
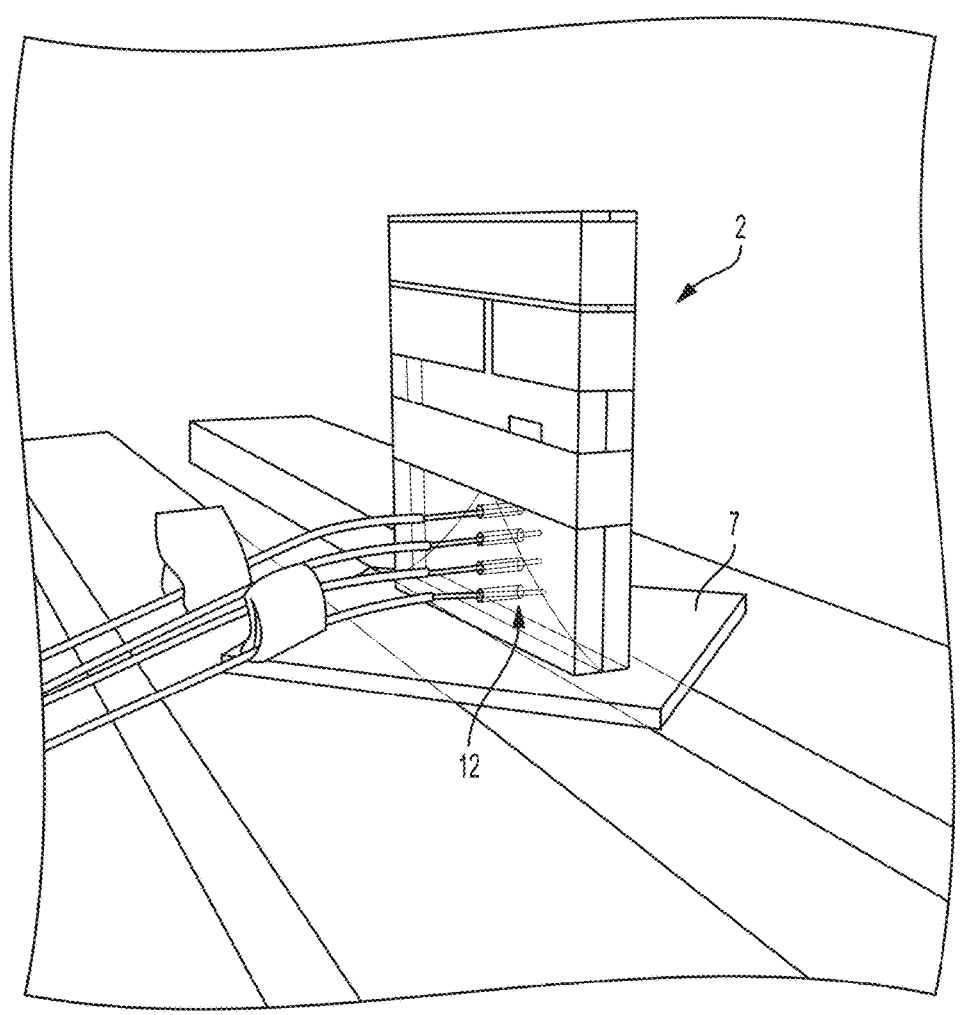
FIG. 5 is a perspective view of the test fixture of FIG. 4.

As shown in FIGS. 4 and 5, a test fixture 2 is provided for supporting a shaped charge 4. In one embodiment, test fixture 2 is comprised of a polymeric material, for example an acrylic material, however, other materials may be used for test fixture 2. Text fixture 2 includes a perimeter frame or wall 6, a base 7, and a support wall 8, all of which support shaped charge 4. Additionally, text fixture 2 includes a plurality of rate pin holes 10 positioned generally opposite support wall 8 and below shaped charge 4. Illustratively, test fixture 2 includes five rate pin holes 10, however, alternative embodiments of test fixture 2 may include any number of rate pin holes 10. Each rate pin hole 10 is linearly aligned with adjacent rate pin holes 10 and is configured to receive a rate pin 12, as shown in FIG. 5 and discussed further herein. The design of test fixture 2 may be changed to accommodate different designs of shaped charge 4.

Figure 4A:
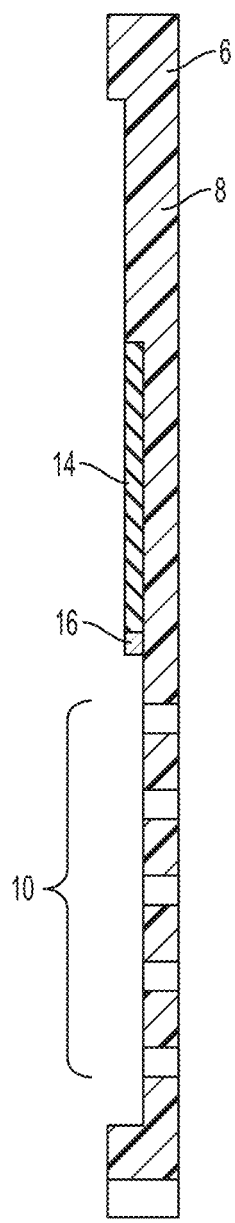
FIG. 4A is a cross-sectional view of the test charge and test fixture of FIG. 4.

Referring to FIGS. 4 and 4A, shaped charge 4 includes explosive material 14 and a two-dimensional shaped liner 16. Illustratively, explosive material 14 is a sheet explosive which contains approximately 1-10 wt. % of explosive material relative to a complete and full-sized explosive which contains at least 50% explosive matter. More particularly, in one embodiment, explosive material 14 includes approximately 2-5 wt. % of explosive material relative to a complete explosive. Alternatively, explosive material 14 may include 1-10%, by volume, of explosive matter relative to a full-size explosive which contains at least 50%, by volume, of explosive matter. In this way, the explosive event resulting from explosive material 14 is minimized because of the reduced quantity of explosive matter within explosive material 14. Additionally, explosive material is coupled to a detonator 32 (FIG. 8) for activating explosive material 14 to conduct a test of shaped charge 4.

In one embodiment, explosive material 14 has the shape of a sideways or horizontally-oriented hourglass in which an upper surface 18 of explosive material 14 defines a chevron or V-shaped cutout 20. As shown in FIG. 4, support wall 8 of test fixture 2 has a complementary shape which couples with upper surface 18 of explosive material 14. Additionally, an upper portion of perimeter wall 6 supports a portion of upper surface 18. Similarly, a lower surface 22 of explosive material 14 defines a chevron or upside-down V-shaped cutout 24. Side walls 26 of explosive material 14 are supported by corresponding side walls of test fixture 2.

With reference to FIGS. 4 and 4A, shaped charge 4 also includes shaped liner 16 which is coupled to explosive material 14. Illustrative shaped liner 16 is a two-dimensional sample with an upside-down V configuration that complements the shape of lower surface 22 of explosive material 14. More particularly, shaped liner 16 is positioned within cutout 24 and is coupled to lower surface 22 of explosive material 14. Rate pin holes 10 also are positioned within cutout 24 and extend toward a peak or crest 28 of shaped liner 16. In one embodiment, shaped liner 16 is comprised of a metallic material and, illustratively, is comprised of aluminum.

Figure 6:
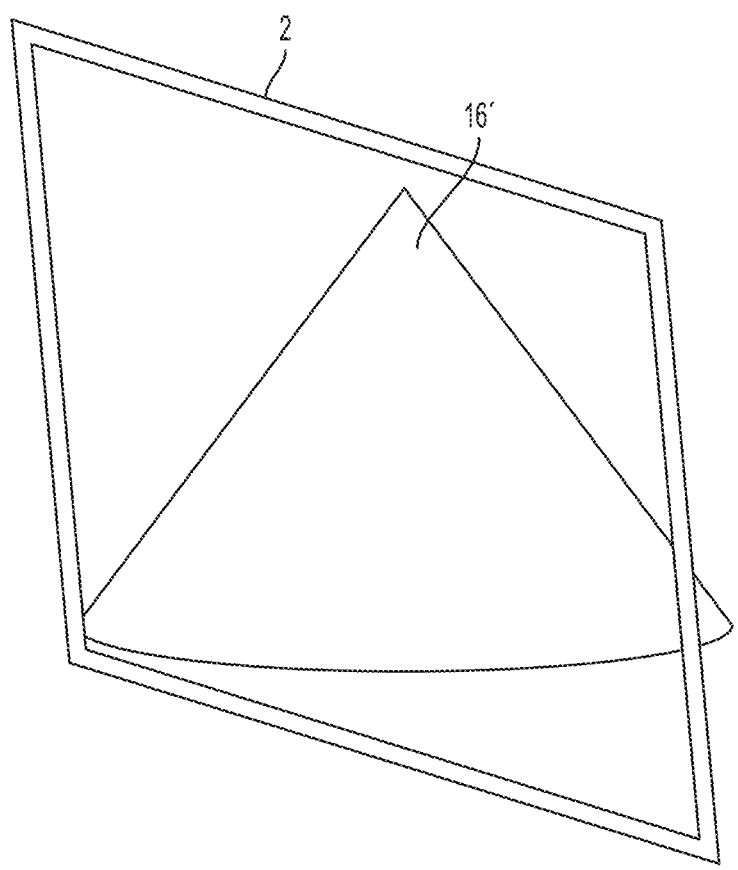
FIG. 6 is a computer model of a three-dimensional test charge positioned within the test fixture of FIG. 4.
Figure 7:
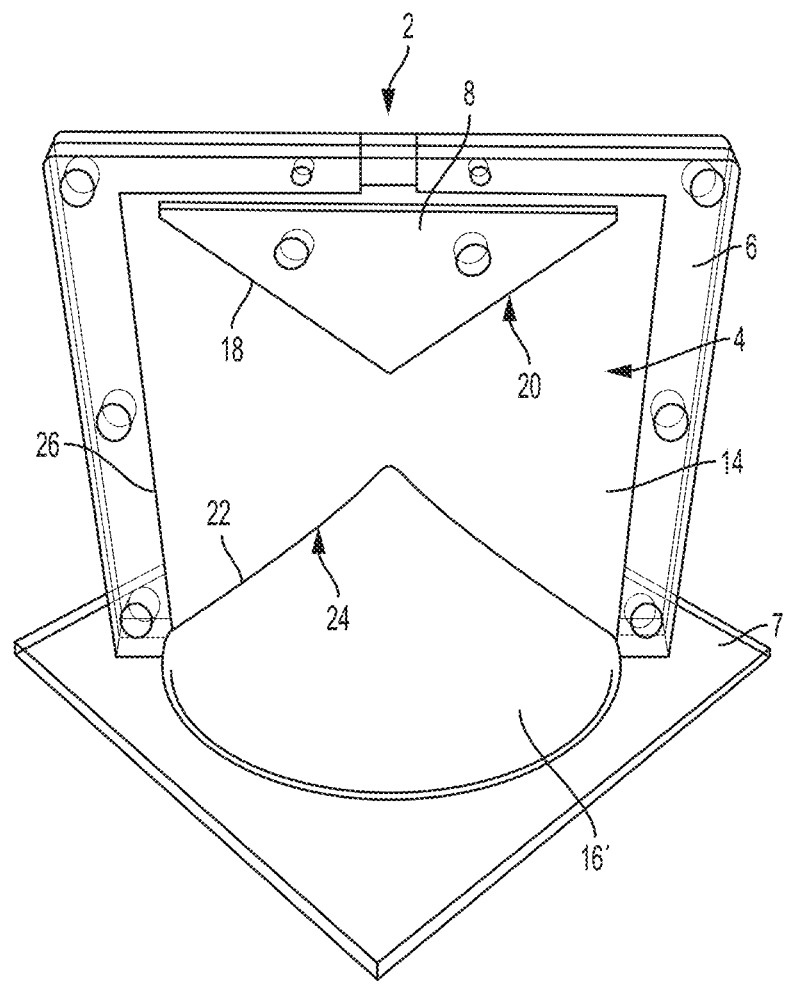
FIG. 7 is a perspective view of a physical sample of the three-dimensional test charge positioned within the test fixture of FIG. 4.

Referring to FIGS. 6 and 7, an alternative embodiment of shaped liner 16 is shown as shaped liner 16'. Unlike two-dimensional shaped liner 16 of FIG. 4, shaped liner 16' of FIGS. 6 and 7 is three-dimensional and defines a cone shape. Shaped liner 16' may define a hollow cone with a cross-sectional shape replicating the shape of shaped liner 16 (FIG. 4). Illustrative shaped liner 16' may be comprised of a metallic material, for example, aluminum, although other material may be used. Similar to shaped liner 16, shaped liner 16' is coupled to lower surface 22 of explosive material 14. Additionally, shaped liner 16' is supported by base 7 of test fixture 2.

In one embodiment, shaped liners 16, 16' may be marked with reference points (not shown) in order to further monitor deflection during an explosive event. The reference points may be notches or etched marks or may be made with permanent marker or another object and are placed in such a way that the reference points do not impact the structural integrity of shaped liners 16, 16' during an explosive test. The reference points provide a method for tracking deformation of liner 16, 16'.

Figure 8:
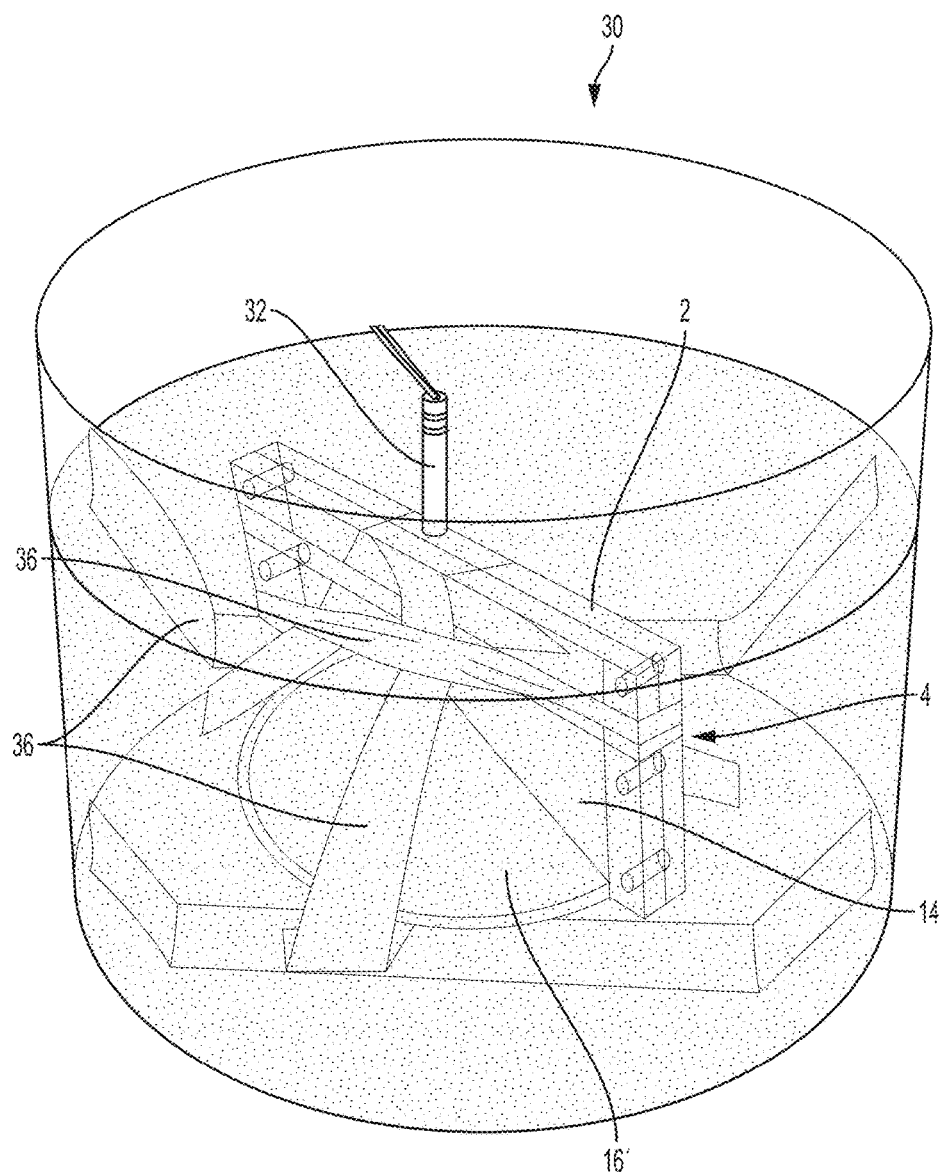
FIG. 8 is a perspective view of the three-dimensional test charge and the test fixture of FIG. 7 placed under water prior to an explosive event.

Referring to FIG. 8, in order to conduct an explosive test on shaped charge 4 and recover shaped liner 16 or 16', shaped charge 4 is positioned within test fixture 2 and explosive material 14 is coupled to detonator 32. The assembled test fixture 2 with shaped charge 4 is then placed in a container 30 of fluid, for example water. There is sufficient fluid within container 30 to fully submerge the assembly of test fixture 2 and shaped charge 4 and to contain the blast of the explosive event. The water level within container 30 may change to accommodate test fixtures 2 and shaped charges 4 with varying sizes. An outside support member 36 may be included to stabilize test fixture 2 within the fluid. For example, outside support member 36 may be tape, clamps, or other devices to stabilize and support test fixture 2 within container 30. In one embodiment, container 30 may include a lid which forms an air-tight seal against the side walls of container 30. Additionally, any air within container 30 and above the fluid level may be removed from container 30 (e.g., through vacuum).

Once shaped charge 4 and test fixture 2 are positioned below the fluid level in container 30, detonator 32 activates explosive material 14 and an explosive test event occurs. During the explosive test event, explosive material 14 is fully consumed and test fixture 2 may be damaged or destroyed, however, shaped liner 16 or 16' is retained within container 30 and can be retrieved from the fluid for metallurgical and/or other testing. In this way, analysis can be performed on an actual physical sample of shaped liner 16 or 16' following the explosive test event to investigate early-stage deformation and reaction of shaped liner 16, 16'.

Figure 9:
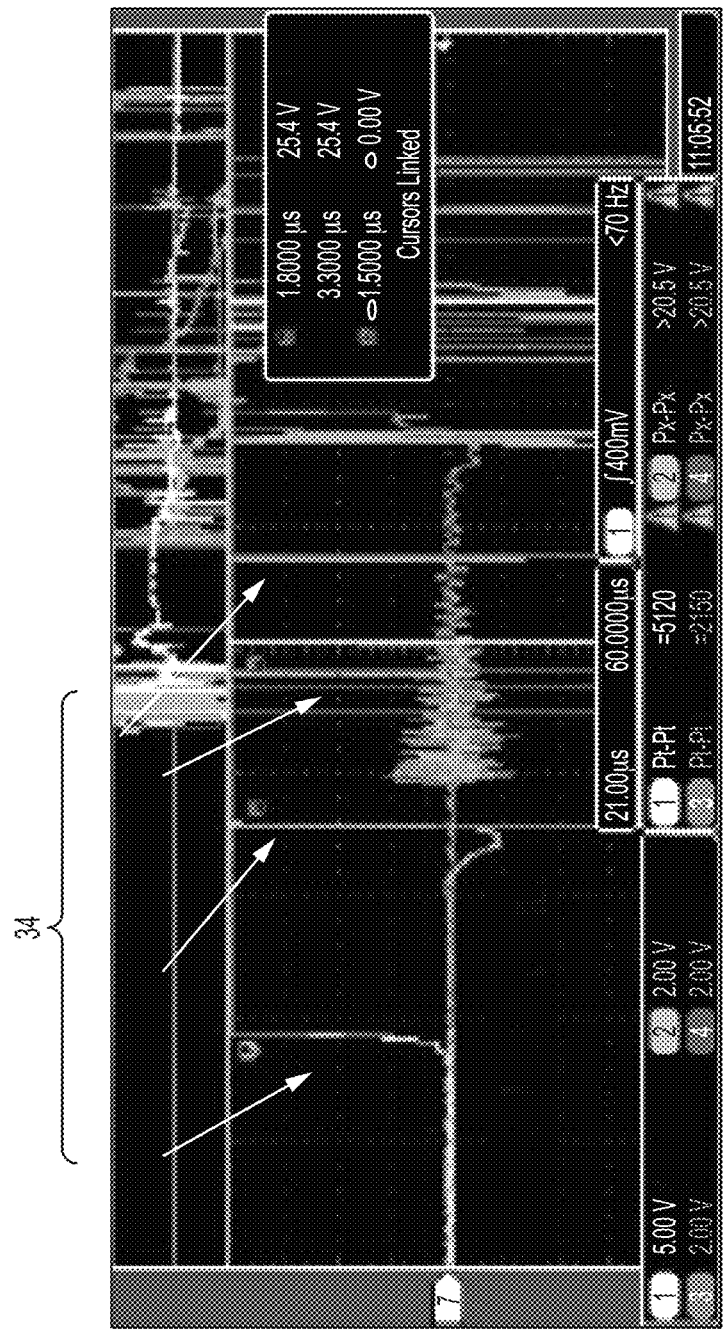
FIG. 9 shows an exemplary output of data from a plurality of rate pins during an explosive event.

Additional information about the reaction of shaped liner 16, 16' during the explosive event may be collected from rate pins 12 (FIG. 5) which are coupled to a measuring device. More particularly, rate pins 12 are supported within rate pin holes 10 during an explosive event and measure the passing of shaped liner 16, 16', as shown in FIG. 9. For example, the location of each rate pin 12 is known and, as such, the velocity of liner 16, 16' as liner 16, 16' passes each rate pin 12 can be calculated with the time differential between each rate pin 12. As shown in FIG. 9, the data recorded by rate pins 12 is shown as vertical peaks or lines 34 on the data chart.

In order to be able to recover shaped liner 16, 16' from container 30 for further analysis, liner 16, 16' does not fully form a shaped charge jet because the explosive material 14 only contains 2-5% of explosive matter relative to a full-size charge. However, the construction of shaped charge 4 within test fixture 2 provides an accurate replication of a typical complex explosive device so that early-stage deformation within shaped liner 16, 16' may be analyzed. As opposed to computer imaging, a use of actual liner material permits experimentation of the actual metallurgical properties of interest because late-stage deformation has not occurred in liner 16, 16' and liner 16, 16' is not destroyed in the explosive test event. Rather, only early-stage deformation occurs and liner 16, 16' is recoverable from container 30 for further analysis.

Figures 10A, 10B:
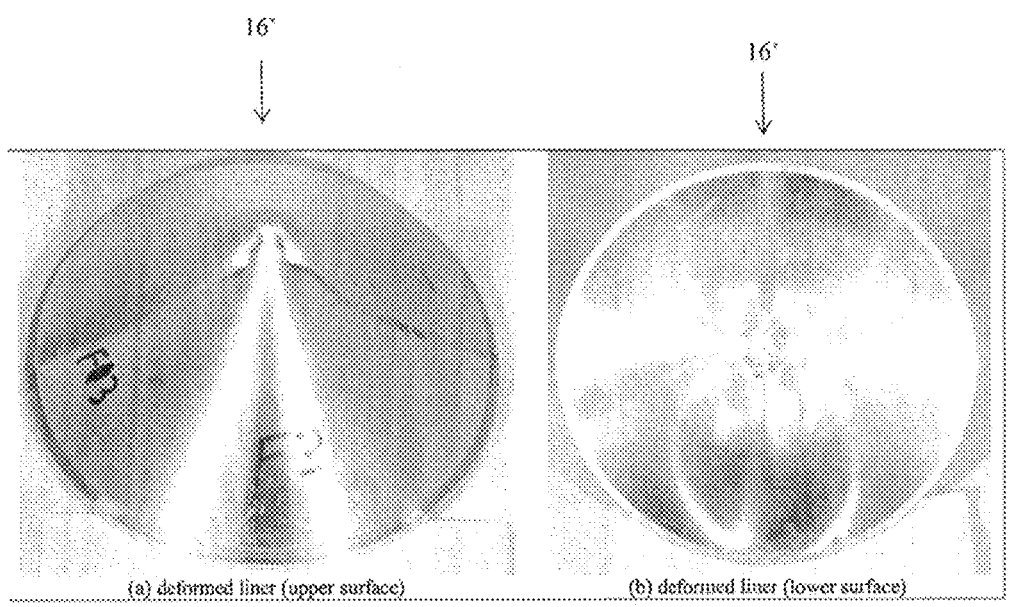
FIG. 10A shows a photograph of an upper surface of the shaped charge liner of FIG. 7 after an explosive event.
FIG. 10B shows a photograph of a lower surface of the shaped charge liner of FIG. 10A after the explosive event.

Referring to FIGS. 10A and 10B, a photograph of shaped liner 16' that is recovered from the aforementioned explosive event shows that the upper surface of shaped liner 16' (FIG. 10A) and the lower surface of shaped liner 16' (FIG. 10B) have deformed and early-stage deformation in the physical sample of liner 16' can be observed. More particularly crest 28 of shaped liner 16' protrudes outwardly as a result of the partially formed shaped charge jet that occurs during an explosive event with a reduced amount of explosive material (e.g., 2-5% explosive matter). In this way, the explosive jets did not fully form and early-stage deformation of shaped liner 16' after an explosive event can be analyzed and a physical sample of shaped liner 16' is available for further testing (e.g., metallurgical analysis). More particularly, with the decreased amount of explosive matter in explosive material 14, liner 16, 16' does not form a plasma slug, which occurs during a full explosive event with a full-sized explosive, in order to recover a deformed liner 16, 16' after the explosive test for further analysis. The present disclosure provides an inexpensive, efficient, and accurate method for investigating early-stage deformation of a liner of a shaped charge.

Although the invention has been described in detail with reference to certain preferred embodiments, variations and modifications exist within the spirit and scope of the invention as described and defined in the following claims.

What is claimed is:

1. A method of analyzing early-stage deformation of a liner of a shaped charge, comprising:
    providing a testing apparatus having an outer wall defining an opening and a support wall extending into the opening;
    assembling a shaped charge including coupling an explosive material to a shaped charge liner, the explosive material comprising approximately 1-10% explosive matter;
    positioning the shaped charge within the opening of the test apparatus, the explosive material being supported by the outer wall and the support wall of the testing apparatus;
    affixing a detonator to the explosive material;
    positioning the testing apparatus and shaped charge within a container of fluid and below a surface of the fluid;
    coupling at least one retaining member to the testing apparatus within the container of fluid;
    detonating the shaped charge; and
    collecting the liner from the fluid.

2. The method of claim 1, further comprising conducting metallurgical testing on the liner's material.

3. The method of claim 1, further comprising removing air from the container above the surface of the fluid.

4. The method of claim 1, wherein the explosive material includes 2-5% explosive matter.

5. The method of claim 1, wherein the liner is comprised of aluminum.

6. The method of claim 1, further comprising assembling a plurality of rate pins to the testing apparatus and detecting, with the rate pins, a change in the liner during the step of detonating the shaped charge.

7. The method of claim 1, wherein the liner defines a three-dimensional cone shape.

8. The method of claim 1, wherein the liner defines a two-dimensional chevron shape.

9. The method of claim 1, wherein the explosive material defines a first chevron-shaped cutout and a second chevron-shaped cutout, and the support wall of the testing apparatus is configured to be positioned within the first chevron-shaped cutout and the liner's material is configured to be positioned within the second chevron-shaped cutout.

10. A method of analyzing early-stage deformation of a liner of a shaped charge, comprising:
    providing a testing apparatus having an outer wall defining an opening and a support wall extending into the opening;
    assembling a shaped charge including coupling an explosive material to a shaped charge liner, the explosive material comprising approximately 1-10% explosive matter;
    positioning the shaped charge within the opening of the test apparatus, the explosive material being adjacent the outer wall and the support wall of the testing apparatus;
    affixing a detonator to the explosive material;
    disposing the testing apparatus containing the shaped charge within a fluid;
    detonating the shaped charge; and
    collecting the liner from the fluid.

11. The method of claim 10, wherein the shaped charge is formed so that the detonating step results in a partial jet formation.

12. The method of claim 11, further comprising analyzing early-stage deformation in the liner's material after the partial jet formation.

13. The method of claim 10, further comprising conducting metallurgical testing on the liner's material.

14. The method of claim 10, further comprising positioning the testing apparatus and shaped charge in a container of fluid prior to the detonating step.

15. The method of claim 10, wherein the explosive material includes 2-5% explosive matter.

16. The method of claim 10, wherein the liner is comprised of aluminum.

17. The method of claim 10, further comprising assembling a plurality of rate pins to the testing apparatus and detecting, with the rate pins, a change in the liner's material during the step of detonating the shaped charge.

18. The method of claim 10, wherein the liner defines a three-dimensional cone shape.

19. The method of claim 10, wherein the liner defines a two-dimensional chevron shape.

20. The method of claim 10, wherein the testing apparatus is comprised of a polymeric material.

21. A test assembly configured for analyzing a shaped charge during an explosive event, comprising:
- a test fixture including a frame having a generally rectangular shape, a support wall extending within the frame, and a plurality of rate holes positioned generally opposite the support wall;
- an explosive sheet comprised of 1-10% explosive matter and coupled to the frame; and
- a shaped liner coupled to the explosive sheet and positioned above the plurality of rate holes.

22. The test assembly of claim 21, wherein the test fixture is comprised of an acrylic material.

23. The test assembly of claim 21, wherein the shaped liner is comprised of aluminum.

24. The test assembly of claim 21, wherein the each of the rate holes is configured to receive a rate pin, and the rate pin is configured to determine a change within the shaped liner during an explosive event.

25. The test assembly of claim 21, further comprising a container of fluid configured to receive the test fixture, the explosive sheet, and the shaped liner.

* * * * *